(12) United States Patent
Müller et al.

(10) Patent No.: US 7,244,692 B2
(45) Date of Patent: Jul. 17, 2007

(54) SUBSTITUTED BENZOYLCYCLOHEXANE DIONES FOR USE AS HERBICIDES

(75) Inventors: Klaus-Helmut Müller, Düsseldorf (DE); Hans-Georg Schwarz, Langenfeld (DE); Stefan Lehr, Langenfeld (DE); Otto Schallner, Monheim (DE); Dorothee Hoischen, Monheim (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 245 days.

(21) Appl. No.: 10/945,510

(22) Filed: Sep. 20, 2004

(65) Prior Publication Data

US 2005/0054534 A1    Mar. 10, 2005

Related U.S. Application Data

(62) Division of application No. 10/168,420, filed as application No. PCT/EP00/12583 on Dec. 12, 2000, now Pat. No. 6,825,183.

(30) Foreign Application Priority Data

Dec. 24, 1999  (DE) ............... 199 62 923

(51) Int. Cl.
C07D 239/10 (2006.01)
A01N 43/54 (2006.01)
C07D 233/32 (2006.01)

(52) U.S. Cl. .............. 504/242; 544/315; 544/318

(58) Field of Classification Search ............. 544/315, 544/318; 504/242
See application file for complete search history.

(56) References Cited

U.S. PATENT DOCUMENTS

| 2,518,264 | A | 8/1950 | Abramovitch | 260/309.6 |
| 3,833,586 | A | 9/1974 | Schwan et al. | 260/251 R |
| 5,852,192 | A | 12/1998 | Himmelsbach et al. | 546/210 |
| 6,004,903 | A | 12/1999 | vn Deyn et al. | 504/239 |
| 6,153,759 | A | 11/2000 | von Deyn et al. | 548/131 |

FOREIGN PATENT DOCUMENTS

| DE | 199 21 732 | 1/2000 |
| EP | 0 058 868 | 9/1982 |
| EP | 0 135 191 | 10/1988 |
| EP | 0 186 120 | 11/1988 |
| EP | 0 186 119 | 8/1989 |
| EP | 0 090 262 | 8/1992 |
| EP | 0 319 075 | 7/1994 |
| GB | 1327552 | 8/1973 |
| WO | 94/22826 | 10/1994 |
| WO | 95/03450 | 12/1995 |
| WO | 97/46530 | 12/1997 |
| WO | 99/07688 | 2/1999 |

OTHER PUBLICATIONS

J. Amer. Chem. Soc., 78, Oct. 20, 1956, "Chemotherapeutic Nitrofurans. IV. Some Derivatives of 1-Amino-2-imidazolidinone, 1-Amino-2-pyrrolidinone and 3-Amino-2-thiazolidinone", Julian G. Michels and Gabriel Gever, pp. 5349-5351.

Experientia, 13, (month unavailable) 1957, Brèves communications—Kurze Mitteilungen Brevi communicazioni—Brief Reports, p. 183.

Chem. Pharm. Bull., vol. 28, (month unavailable) 1980, pp. 1810-1813, "Synthesis in the Diazasteroid Group. XIV.[1]) Synthesis of the 13,15-Diazasteroid System", Katsuhide Matoba, Toshio Imai, Yoshie Nishino, Hiroki Takahata, Yoshiro Hirai and Takao Yamazaki.

J. Chem. Soc. Perkin Trans. 1, (month unavailable) 1998, pp. 423-436, "Linear and macrocyclic ligands containing alternating pyridine and imidazolidin-2-one units", Otto Meth-Cohn and Zegui Yan.

Synthesis, Dec. 1978, pp. 925-927, "A New Simple Synthesis of 2-Acylcyclohexane-1,3-diones", A.A. Akhrem, F.A. Lakhvich, S.I. Budai, T.S. Khlebencova, I.I. Petrusevich.

Tetrahedron Letters, vol. 37, No. 7, (month unavailable), 1996, pp. 1007-1010, "The Cyanide Catalyzed Isomerization of Enol Esters Derived from Cyclic 1,3-Diketones", Imber Flores Montes and Ulrich Burger.

(Continued)

Primary Examiner—Deepak Rao
(74) Attorney, Agent, or Firm—Richard E. L. Henderson

(57) ABSTRACT

The invention relates to novel substituted benzoylcyclohexanediones of formula (I)

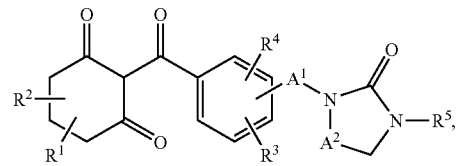

(I)

in which
A$^1$ represents a single bond or represents alkanediyl (alkylene) having 1 to 3 carbon atoms,
A$^2$ represents alkanediyl (alkylene) having 1 to 3 carbon atoms, and
R$^1$, R$^2$, R$^3$, R$^4$ and R$^5$ are each as defined in the disclosure, and to novel intermediates, to processes for their preparation and to their use as herbicides.

9 Claims, No Drawings

OTHER PUBLICATIONS

Database Chemabs Online! Chemical Abstracts Service, Columbus, Ohio, US; Ogawa, Hidenori et al: "Preparation and formulaltion of benzazepine derivatives and analogs as pharmaceuticals with affinity for vasopressin receptors" retrieved from STN Database accession No. 127:248027 XP002162488 compounds with RN=175152-96-2; 175152-96-2; 175152-97-3; 175153-46-5; 195507-70-1 & JP 09 221476 A (Otsuka Pharmaceutical Co., Ltd., Japan) Aug. 26, 1997.

Database Chemabs 'Online! Chemical Abstracts Service, Columbus, Ohio, US; Babczinski, Peter et al: "Substituted tetrahydropyrimidiones: a new herbicidal class of compounds inducing chlorosis by inhibition of phytoene desaturation. 2. Structure-activity relationships" retrieved from STN Database accession No. 123:49747 XP002162489 compound with RN=164793-71-9 & Pestic. Biochem. Physiol. (1995), 52(1), 45-59.

Database Chemabs Online! Chemical Abstracts Service, Columbus Ohio, US, Nagarajan, K. et al: "Nitroimidazoles. Part IV. 1-Sulfonyl(carbamoyl/thiocarbamoyl)-3-(1-methyl-5-nitroimidazol-2-yl)-2-imidazolidinones" retrived from STN Database accession No. 98:215526 XP002162491 compound with RN=85695-19-8 das ganze Dokument & Indian J. Chem., Sect. B (1982), 21B(10), 928-40.

Database Chemabs 'Online! Chemical Abstracts Service, Columbus, Ohio, US; Cram, Donald J. et al: "Strongly binding, rapidly complexing, ion selective spherands" retrieved from STN Database accession No. 98:53855 XP002162492 compound with RN=84395-43-7 & J. Chem. Soc., Chem. Commun. (1982), (21), 1219-21.

Database Chemabs 'Online! Chemical Abstracts Service, Columbus, Ohio, US: Cram, D J. et al: "Host-guest complexation. 32. Spherands composed of cyclic urea and anisyl units" retrieved from STN Database accession No. 101:210478 XP002162751 compounds with RN=84395-43-7; 92185-84-7; 92185-83-6 & J. Am. Chem. Soc. (1984), 106(23), 7150-67.

SUBSTITUTED BENZOYLCYCLOHEXANE DIONES FOR USE AS HERBICIDES

This application is a division of U.S. application Ser. No. 10/168,420, filed Jun. 21, 2002, now U.S Pat. No. 6,825,183, which was filed under 35 U.S.C. 371 as a national stage application of International Application No. PCT/EP00/12583, filed Dec. 12, 2000, which was published in German as International Patent Publication WO 01/47894 on Jul. 5, 2001, which is entitled to the right of priority of German Patent Application No. 199 62 923.4, filed Dec. 24,1999.

BACKGROUND OF THE INVENTION

The invention relates to novel substituted benzoylcyclohexanediones, to processes for their preparation and to their use as herbicides.

It is already known that certain substituted benzoylcyclohexanediones have herbicidal properties (cf. EP-A-090262, EP-A-135191, EP-A-186118, EP-A-186119, EP-A-186120, EP-A-319075, DE-A-199 21 732, WO-A-96/26200, WO-A-97/46530, WO-A-99/07688). However, the activity of these compounds is not in all respects satisfactory.

Further substituted benzoylcyclohexanediones are part of the subject-matter of an earlier, but not prior-published, patent application (cf. DE-A 19 921 732).

DETAILED DESCRIPTION OF THE INVENTION

This invention, accordingly, provides the novel substituted benzoylcyclohexanediones of the general formula (I)

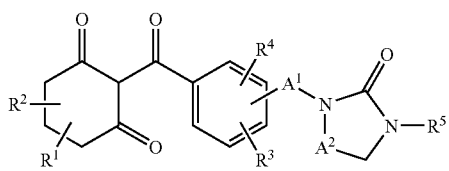

in which
- $A^1$ represents a single bond or represents alkanediyl (alkylene) having 1 to 3 carbon atoms,
- $A^2$ represents alkanediyl (alkylene) having 1 to 3 carbon atoms,
- $R^1$ represents hydrogen, represents phenyl or represents in each case optionally halogen-substituted alkyl, alkylthio or alkoxycarbonyl having in each case 1 to 4 carbon atoms in the alkyl groups,
- $R^2$ represents hydrogen or represents in each case optionally halogen-substituted alkyl or alkylthio having in each case 1 to 4 carbon atoms, or together with $R^1$ represents alkanediyl (alkylene) having up to 4 carbon atoms, or—if $R^1$ and $R^2$ are attached to the same carbon atom—together with $R^1$ and the carbon atom to which $R^1$ and $R^2$ are attached represents a carbonyl grouping (C=O),
- $R^3$ represents hydrogen, nitro, cyano, carboxyl, carbamoyl, thiocarbamoyl, halogen, represents in each case optionally halogen-substituted alkyl, alkoxy, alkylthio, alkylsulphinyl, alkylsulphonyl, alkylamino, dialkylamino, alkylsulphonylamino or dialkylaminosulphonyl having in each case 1 to 4 carbon atoms in the alkyl groups, or represents in each case optionally halogen- or $C_1$-$C_4$-alkyl-substituted cycloalkylamino, cycloalkylsulphonyl, cycloalkylsulphonylamino or cycloalkylaminosulphonyl having in each case 3 to 6 carbon atoms,
- $R^4$ represents hydrogen, nitro, cyano, carboxyl, carbamoyl, thiocarbamoyl, halogen, or represents in each case optionally halogen-substituted alkyl, alkoxy, alkylthio, alkylsulphinyl, alkylsulphonyl, alkylamino, dialkylamino or dialkylaminosulphonyl having in each case 1 to 4 carbon atoms in the alkyl groups, and
- $R^5$ represents hydrogen, represents amino, represents in each case optionally amino-, cyano-, halogen- or $C_1$-$C_4$-alkoxy-substituted alkyl, alkoxy, alkyl-amino, dialkylamino, alkylsulphonyl or alkylsulphonylamino having in each case 1 to 5 carbon atoms in the alkyl groups, represents in each case optionally halogen-substituted alkenyl or alkinyl having in each case up to 5 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and optionally 1 to 3 carbon atoms in the alkyl moiety, represents cycloalkenyl having 5 or 6 carbon atoms, or represents in each case optionally nitro-, cyano-, carboxyl-, halogen-, $C_1$-$C_4$-alkyl-, $C_1$-$C_4$-halogenoalkyl-, $C_1$-$C_4$-alkoxy- or $C_1$-$C_4$-halogenoalkoxy-substituted phenyl, phenyl-$C_1$-$C_4$-alkyl, pyridyl or pyrimidinyl, except for the compound 1-[2,6-dichloro-3-[(2-hydroxy-6-oxo-cyclohexen-1-yl)-carbonyl]-benzyl]-3-methyl-tetrahydro-2(1H)-pyrimidinone (cf. DE-A 19 921 732, Table 2, Example ID-1).

The invention also provides all possible tautomeric forms of the compounds of the general formula (I) and the possible salts and metal complexes of the compounds of the general formula (I).

In the definitions, the hydrocarbon chains, such as alkyl or alkanediyl, are in each case straight-chain or branched—including in combination with hetero atoms, such as in alkoxy.

In addition to the compounds of the general formula (I)—above—it is in each case also possible for the corresponding tautomeric forms—shown in exemplary manner below—to be present.

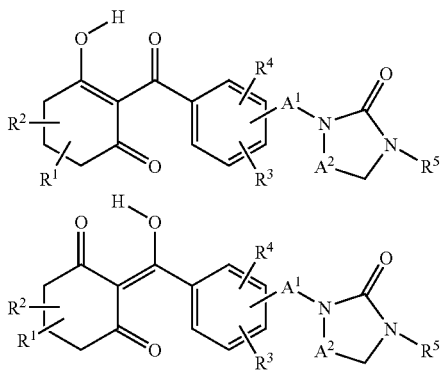

Preferred meanings of the radicals/substituents listed in the formulae shown above are illustrated below.

$A^1$ preferably represents a single bond, represents methylene, ethane-1,1-diyl (ethylidene), ethane-1,2-diyl (dimethylene), propane-1,1-diyl, propane-1,2-diyl or propane-1,3-diyl.

$A^2$ preferably represents methylene, ethane-1,1-diyl (ethylidene), ethane-1,2-diyl (dimethylene), propane-1,1-diyl, propane-1,2-diyl or propane-1,3-diyl.

$R^1$ preferably represents hydrogen, represents phenyl or represents in each case optionally fluorine- and/or chlorine-substituted methyl, ethyl, n- or i-propyl, methylthio, ethylthio, n- or i-propylthio, methoxycarbonyl, ethoxycarbonyl, n- or i-propoxycarbonyl.

$R^2$ preferably represents hydrogen or represents in each case optionally fluorine- and/or chlorine-substituted methyl, ethyl, n- or i-propyl, methylthio, ethylthio, n- or i-propylthio, or together with $R^1$ represents methylene, ethane-1,1-diyl, ethane-1,2-diyl (dimethylene), propane-1,1-diyl, propane-1,2-diyl or propane-1,3-diyl, or—if $R^1$ and $R^2$ are attached to the same carbon atom—together with $R^1$ and the carbon atom to which $R^1$ and $R^2$ are attached represents a carbonyl grouping (C=O).

$R^3$ preferably represents hydrogen, nitro, cyano, carboxyl, carbamoyl, thiocarbamoyl, fluorine, chlorine, bromine, iodine, represents in each case optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino, diethylamino, methylsulphonylamino, ethylsulphonylamino, n- or i-propylsulphonylamino, dimethylaminosulphonyl or diethylaminosulphonyl, or represents in each case optionally fluorine-, chlorine- or methyl-substituted cyclopropylamino, cyclobutylamino, cyclopentylamino, cyclohexylamino, cyclopropylsulphonyl, cyclobutylsulphonyl, cyclopentylsulphonyl, cyclohexylsulphonyl, cyclopropylsulphonylamino, cyclobutylsulphonylamino, cyclopentylsulphonylamino, cyclohexylsulphonylamino, cyclopropylaminosulphonyl, cyclobutylaminosulphonyl, cyclopentylaminosulphonyl or cyclohexylaminosulphonyl.

$R^4$ preferably represents hydrogen, nitro, cyano, carboxyl, carbamoyl, thiocarbamoyl, fluorine, chlorine, bromine, iodine, or represents in each case optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino, diethylamino, dimethylaminosulphonyl or diethylaminosulphonyl.

$R^5$ preferably represents hydrogen, represents amino, represents in each case optionally amino-, cyano-, fluorine- and/or chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, di-propylamino, methylsulphonyl, ethylsulphonyl or methylsulphonylamino, represents in each case optionally fluorine-, chlorine- and/or bromine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents cyclohexenyl, or represents in each case optionally fluorine-, chlorine-, bromine-, methyl-, trifluoromethyl-, methoxy-, difluoromethoxy- or trifluoromethoxy-substituted phenyl, benzyl, pyridyl or pyrimidinyl.

$A^1$ particularly preferably represents a single bond, represents methylene, ethane-1,2-diyl (dimethylene) or propane-1,3-diyl.

$A^2$ particularly preferably represents methylene, ethane-1,2-diyl (dimethylene) or propane-1,3-diyl.

$R^1$ particularly preferably represents hydrogen, phenyl, -methyl, ethyl, n- or i-propyl, methylthio, ethylthio, methoxycarbonyl or ethoxycarbonyl.

$R^2$ particularly preferably represents hydrogen, methyl, ethyl, methylthio, ethylthio, or together with $R^1$ represents methylene, ethane-1,2-diyl (dimethylene) or propane-1,3-diyl (trimethylene), or—if $R^1$ and $R^2$ are attached to the same carbon atom—together with $R^1$ and the carbon atom to which $R^1$ and $R^2$ are attached represents a carbonyl grouping (C=O).

$R^3$ particularly preferably represents hydrogen, nitro, cyano, fluorine, chlorine, bromine, iodine, represents in each case optionally fluorine- and/or chlorine-substituted methyl, ethyl, methoxy, ethoxy, methylthio, ethylthio, methylsulphinyl, ethylsulphinyl, methylsulphonyl, ethylsulphonyl, represents methylamino, ethylamino, dimethylamino or dimethylaminosulphonyl.

$R^4$ particularly preferably represents hydrogen, nitro, cyano, fluorine, chlorine, bromine, iodine, represents in each case optionally fluorine- and/or chlorine-substituted methyl, ethyl, methoxy, ethoxy, methylthio, ethylthio, methylsulphinyl, ethylsulphinyl, methylsulphonyl, ethylsulphonyl, represents methylamino, ethylamino, dimethylamino or dimethylaminosulphonyl.

$R^5$ particularly preferably represents hydrogen, methyl, ethyl, n- or i-propyl, n-, i-, s- or t-butyl, propenyl, propinyl, cyclopropyl, cyclopentyl, cyclohexyl, cyclopropylmethyl, cyclopentylmethyl, cyclohexylmethyl, phenyl or benzyl.

$A^1$ very particularly preferably represents methylene or ethane-1,2-diyl (dimethylene).

$A^2$ very particularly preferably represents methylene or ethane-1,2-diyl (dimethylene).

$R^1$ very particularly preferably represents hydrogen, phenyl, methyl, ethyl, n- or i-propyl, methylthio or ethylthio.

$R^2$ very particularly preferably represents hydrogen, methyl, ethyl, methylthio, or together with $R^1$ represents ethane-1,2-diyl or propane-1,3-diyl, or—if $R^1$ and $R^2$ are attached to the same carbon atom—together with $R^1$ and the carbon atom to which $R^1$ and $R^2$ are attached represents a carbonyl grouping (C=O).

$R^3$ very particularly preferably represents hydrogen, nitro, cyano, fluorine, chlorine, bromine, methyl, difluoromethyl, trifluoromethyl, dichloromethyl, trichloromethyl, chlorodifluoromethyl, ethyl, methoxy, difluoromethoxy, trifluoromethoxy, chlorodifluoromethoxy, ethoxy, methylthio, difluoromethylthio, trifluoromethylthio, chlorodifluoromethylthio, ethylthio, methylsulphinyl, trifluoromethylsulphinyl, ethylsulphinyl, methylsulphonyl, trifluoromethylsulphonyl, ethylsulphonyl, dimethylamino or dimethylaminosulphonyl.

$R^4$ very particularly preferably represents hydrogen, nitro, cyano, fluorine, chlorine, bromine, methyl, difluoromethyl, trifluoromethyl, dichloromethyl, trichloromethyl, chlorodifluoromethyl, ethyl, methoxy, difluoromethoxy, trifluoromethoxy, chlorodifluoromethoxy, ethoxy, methylthio, difluoromethylthio, trifluoromethylthio, chlorodifluoromethylthio, ethylthio, methylsulphinyl, trifluoromethylsulphinyl, ethylsulphinyl, methylsulphonyl, trifluoromethylsulphonyl, ethylsulphonyl, dimethylamino or dimethylaminosulphonyl.

$R^5$ very particularly preferably represents hydrogen, methyl, ethyl, n- or i-propyl, n-, i-, s- or t-butyl, cyclopropyl, cyclopentyl or cyclohexyl.

The invention also preferably provides sodium, potassium, magnesium, calcium, ammonium, $C_1$-$C_4$-alkyl-ammonium, di-($C_1$-$C_4$-alkyl)-ammonium, tri-($C_1$-$C_4$-alkyl)-ammonium, tetra-($C_1$-$C_4$-alkyl)-ammonium, tri-($C_1$-$C_4$-alkyl)-sulphonium, $C_5$- or $C_6$-cycloalkyl-ammonium and di-($C_1$-$C_2$-alkyl)-benzyl-ammonium salts of compounds of the formula (I) in which $A^1$, $A^2$, $R^1$, $R^2$, $R^3$, $R^4$ and $R^5$ are each as defined above, or else complex compounds (coordination compounds) of these compounds with metals such as copper, iron, cobalt, nickel.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

The abovementioned general or preferred radical definitions apply both to the end products of the formula (I) and, correspondingly, to the starting materials or intermediates required in each case for the preparation. These radical definitions can be combined with one another if desired, i.e. including combinations between the given preferred ranges.

Compounds of the general formulae (IA), (IB) and (IC) below—where $A^1$, $A^2$, $R^1$, $R^2$, $R^3$ and $R^4$ each have the meaning given above as being very particularly preferred—are particularly emphasized as being according to the invention:

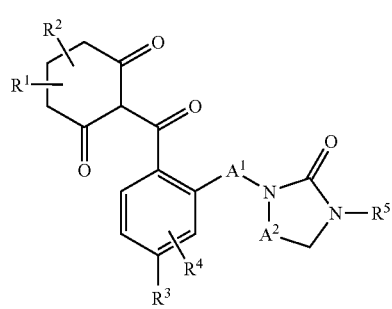

(IA)

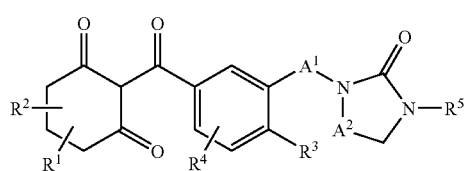

(IB)

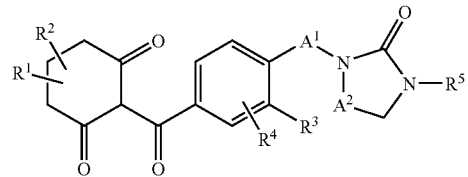

(IC)

The novel substituted benzoylcyclohexanediones of the general formula (I) have strong and selective herbicidal activity.

The novel substituted benzoylcyclohexanediones of the general formula (I) are obtained when 1,3-cyclohexanedione or its derivatives of the general formula (II)

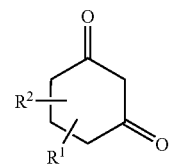

(II)

in which $R^1$ and $R^2$ are each as defined above, are reacted with substituted benzoic acids of the general formula (III)

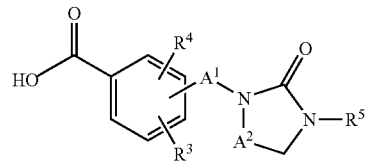

(III)

in which $A^1$, $A^2$, $R^3$, $R^4$ and $R^5$ are each as defined above, in the presence of a dehydrating agent, if appropriate in the presence of one or more reaction auxiliaries and if appropriate in the presence of a diluent.

In principle, the compounds of the general formula (I) can also be synthesized as shown schematically below:

Reaction of 1,3-cyclohexanedione or its derivatives of the general formula (II)—above—with reactive derivatives of the substituted benzoic acids of the general formula (III)—above—in particular with the corresponding carbonyl chlorides, carboxylic anhydrides, carboxylic acid cyanides, carbonyl-imidazolides, carbonyl-triazolides, methyl carboxylates or ethyl carboxylates—if appropriate in the presence of reaction auxiliaries, such as, for example, triethylamine (and, if appropriate, additionally zinc chloride), and, if appropriate, in the presence of a diluent, such as, for example, methylene chloride:

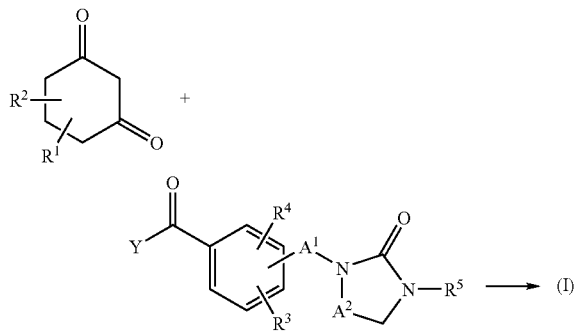

(Y is, for example, CN, Cl, imidazolyl, triazolyl, methoxy, ethoxy)

In the reactions outlined above for preparing the compounds of the general formula (I), there is, in addition to the desired C-benzoylation at the cyclohexanedione, also an O-benzoylation—cf. equation below (cf. Synthesis 1978, 925-927; Tetrahedron Lett. 37 (1996), 1007-1009, WO-A-91/05469). However, the O-benzoyl compounds formed in this process are, under the reaction conditions of the process according to the invention, isomerized to the corresponding C-benzoyl compounds of the formula (I).

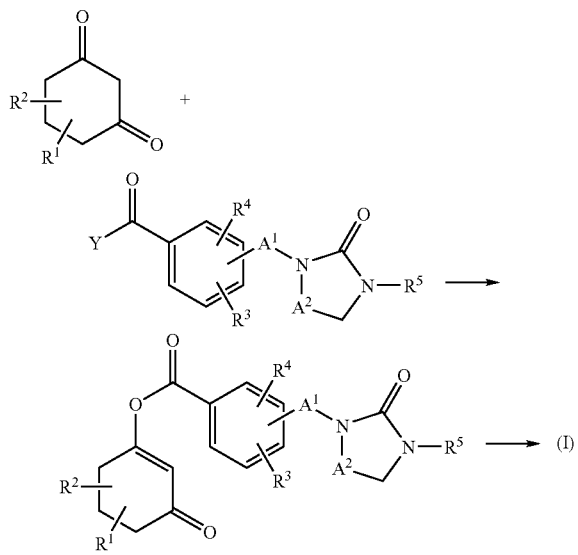

Using, for example, 1,3-cyclohexanedione and 3-fluoro-5-[(3-methyl-2-oxo-imidazolidin-1-yl)-methyl]-benzoic acid as starting materials, the course of the reaction in the process according to the invention can be illustrated by the following equation:

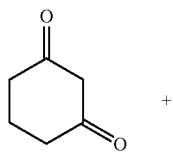

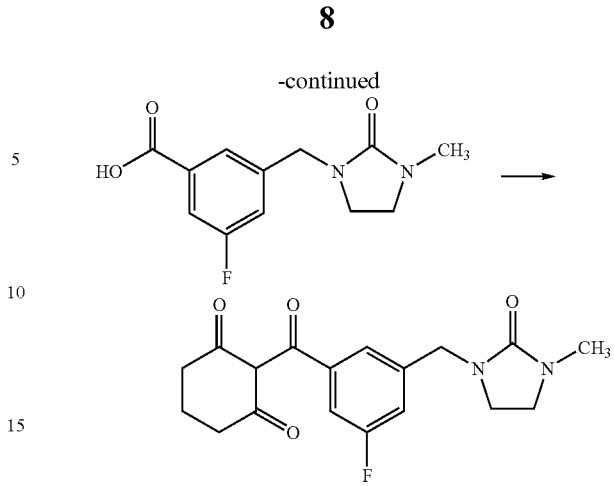

The formula (II) provides a general definition of the cyclohexanediones to be used as starting materials in the process according to the invention for preparing compounds of the general formula (I). In the general formula (II), $R^1$ and $R^2$ each preferably or in particular have those meanings which have already been given above, in connection with the description of the compounds of the general formula (I) according to the invention, as being preferred or as being particularly preferred for $R^1$ and $R^2$.

The starting materials of the general formula (II) are known and/or can be prepared by processes known per se.

The formula (III) provides a general definition of the substituted benzoic acids further to be used as starting materials for the process according to the invention for preparing compounds of the general formula (I). In the general formula (III), $A^1$, $A^2$, $R^3$, $R^4$ and $R^5$ each preferably have those meanings which have already been given above, in connection with the description of the compounds of the general formula (I) according to the invention, as being preferred, as being particularly preferred or as being very particularly preferred for $A^1$, $A^2$, $R^3$, $R^4$ and $R^5$.

The starting materials of the general formula (III) are novel; however, they can be prepared by processes known per se (cf. U.S. Pat. No. 3,833,586, WO-A-94/22826, WO-A-95/34540). Accordingly, the compounds of the formula (III) likewise form part of the subject-matter of the present invention.

The substituted benzoic acids of the general formula (III) are obtained when corresponding substituted benzoic esters of the general formula (IV)

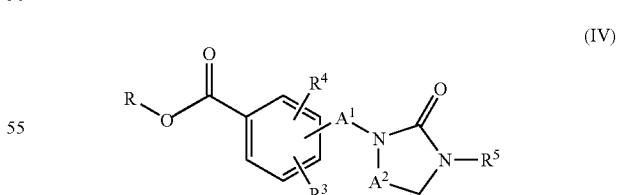

in which $A^1$, $A^2$, $R^3$, $R^4$ and $R^5$ are each as defined above and

R represents alkyl (in particular methyl or ethyl), are reacted with water, if appropriate in the presence of a hydrolysis auxiliary, such as, for example, sodium hydroxide, and if appropriate in the presence of an organic solvent, such as, for example, 1,4-dioxane, at temperatures between 10° C. and 100° C. (cf. the Preparation Examples).

The substituted benzoic esters of the general formula (IV) required as precursors are novel; however, they can be prepared by processes known per se (cf. U.S. Pat. No. 3,833,586, WO-A-94/22826, WO-A-95/34540). Accordingly, the compounds of the formula (IV) also form part of the subject-matter of the present invention.

The substituted benzoic esters of the general formula (IV) are obtained when corresponding halogenoalkylbenzoic esters of the general formula (V)

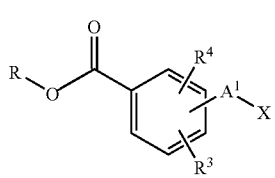

(V)

in which $A^1$, R, $R^3$ and $R^4$ are each as defined above and

X represents halogen (in particular fluorine, chlorine or bromine) or alkylsulphonyloxy (in particular methylsulphonyloxy or ethylsulphonyloxy), are reacted with 1,3-diaza-2-oxo-cycloalkanes of the general formula (VI)

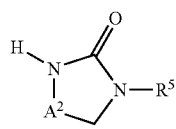

(VI)

in which $A^2$ and $R^5$ are each as defined above, if appropriate in the presence of an acid acceptor, such as, for example, potassium carbonate or sodium carbonate, if appropriate in the presence of a further reaction auxiliary, such as, for example, potassium iodide or sodium iodide, in the presence of a diluent, such as, for example, acetone, acetonitrile or N,N-dimethyl-formamide, at temperatures between 10° C. and 120° C. (cf. the Preparation Examples).

Some of the compounds of the formula (VI) are known (J. Amer. Chem. Soc. 78, 5349, (1956), U.S. Pat. No. 2,518, 264, Experientia 13, 183 (1957), Chem. Pharm. Bull. 1980, 1810, J. Chem. Soc. Perkin Trans 1, 1998, 423, U.S. Pat. No. 5,972,431) and can be prepared as described in these publications. However, some compounds of the formula (VI) are novel (see also Table 5), and they form part of the subject-matter of this application.

The process according to the invention for preparing the novel substituted benzoylcyclohexanediones of the general formula (I) is carried out using a dehydrating agent. Here, suitable dehydrating agents are the customary chemicals which are suitable for binding water.

Examples of these are dicyclohexylcarbodiimide and carbonyl-bis-imidazole.

A particularly suitable dehydrating agent is dicyclohexylcarbodiimide.

The process according to the invention for preparing novel substituted benzoylcyclohexanediones of the general formula (I) is, if appropriate, carried out using a reaction auxiliary.

Examples of these are sodium cyanide, potassium cyanide, acetone cyanohydrin, 2-cyano-2-(trimethylsilyloxy)-propane, trimethylsilyl cyanide, and 1,2,4-triazole.

The particularly suitable further reaction auxiliary is trimethylsilyl cyanide.

The process according to the invention for preparing the novel substituted benzoylcyclohexanediones of the general formula (I) is, if appropriate, carried out using a further reaction auxiliary. Suitable further reaction auxiliaries for the process according to the invention are, in general, basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo [4,3,0]-non-5-ene (DBN), or 1,8-diazabicyclo[5,4,0]-undec-7-ene (DBU).

Suitable diluents for carrying out the process according to the invention are, in particular, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane or 1,2-dichloro-ethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethylsulphoxide.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a dehydrating agent, and the reaction mixture is generally stirred at the required temperature for several hours. Work-up is carried out by customary methods (cf. the Preparation Examples).

The active compounds according to the invention can be used as defoliants, desiccants, haulm killers and, especially, as weedkillers. By weeds in the broadest sense, there are to be understood all plants which grow in locations where they are not wanted. Whether the substances according to the invention act as total or selective herbicides depends essentially on the amount used. The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

Depending on the concentration, the active compounds according to the invention are suitable for total weed control, for example on industrial sites and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including transgenic plants and including plant varieties which may or may not be protected by plant variety protection rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also-roots, tubers and rhizomes. Parts of plants also include crops, and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by single- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve crop plant compatibility ("safeners"), finished formulations or tank mixes being possible. Also possible are mixtures with compositions for controlling weeds comprising one or more known herbicides and a safener.

Possible components for the mixtures are known herbicides, for example acetochlor, acifluorfen(-sodium), aclonifen, alachlor, alloxydim(-sodium), ametryne, amicarbazone, amidochlor, amidosulfuron, anilofos, asulam, atrazine, azafenidin, azimsulfuron, BAS-662H, beflubutamid, benazolin(-ethyl), benfuresate, bensulfuron(-methyl), bentazone, benzfendizone, benzobicyclon, benzofenap, benzoylprop(-ethyl), bialaphos, bifenox, bispyribac(-sodium), bromobutide, bromofenoxim, bromoxynil, butachlor, butafenacil(-allyl), butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinidon(-ethyl), cinmethylin, cinosulfueron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, desmedipham, diallate, dicamba, dichlorprop(-P), diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron(-methyl), ethofumesate, ethoxyfen, ethoxysulfuron, etobenzanid, fenoxaprop(-P-ethyl), fentrazamide, flamprop(-isopropyl, -isopropyl-L, -methyl), flazasulfuron, florasulam, fluazifop (-P-butyl), fluazolate, flucarbazone(-sodium), flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-butoxypropyl, -meptyl), flurprimidol, flurtamone, fluthiacet (-methyl), fluthiamide, fomesafen, foransulfuron, glufosinate(-ammonium), glyphosate-(-isopropylammonium), halosafen, haloxyfop(-ethoxyethyl, -P-methyl), hexazinone, imazamethabenz-(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron(-methyl), prometryn, propachlor, propanil, propaquizafop, propiso-chlor, procarbazone(-sodium), propyzamide, prosulfocarb, prosuifuiron, pyraflufen(-ethyl), pyrazogyl, pyrazolate, pyrazosulfuron(-ethyl), pyrazoxyfen, pyribenzoxim, pyributicarb, pyridate, pyridatol, pyriftalid, pyriminobac(-methyl), pyrithiobac(-sodium), quinchlorac, quinmerac, quinoclamine, quizalofop(-P-ethyl, -P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifen-sulfuron(-methyl), thiobencarb, tiocarbazil, tralkoxydim, triallate, triasulfuron, tribenuron(-methyl), triclopyr, tridiphane, trifluralin, trifloxysulfuron, triflusulfuron(-methyl) and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

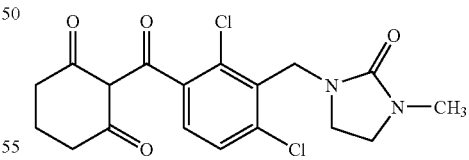

4.4 g (14.5 mmol) of 2,4-dichloro-3-[(3-methyl-2-oxo-imidazolidin-1-yl)-methyl]-benzoic acid are initially charged in 130 ml of acetonitrile and, at room temperature (approximately 20° C.) and with stirring, admixed successively with 2.0 g (17.4 mmol) of 1,3-cyclohexanedione and 3.6 g (17.4 mmol) of dicyclohexylcarbodiimide. The reaction mixture is stirred for 30 minutes and then admixed with 4.4 g (4.35 mmol) of triethylamine and 2.6 g (29 mmol) of acetone cyanohydrin. The mixture is stirred for 15 hours and then filtered, the filtrate is concentrated under waterpump vacuum, the residue is shaken with methylene chloride/1N hydrochloric acid, the organic phase is separated off, admixed with 100 ml of water and adjusted to pH 11 using potassium carbonate and the aqueous phase is shaken with methylene chloride, separated, admixed with 100 ml of methylene chloride and acidified with 1N hydrochloric acid. The organic phase is washed with water and then with saturated aqueous sodium chloride solution, dried with sodium sulphate and filtered. The solvent is carefully distilled off under reduced pressure from the filtrate.

This gives 2.4 g (42% of theory) of 2-[2,4-dichloro-3-[(3-methyl-2-oxo-imidazolidin-1-yl)-methyl]-benzoyl]-1,3-cyclohexanedione as an amorphous product.

Analogously to Example 1, and in accordance with the general description of the preparation process according to the invention, it is also possible to prepare, for example, the compounds of the general formula (I)—or of the formulae (IA), (IB) or (IC)—listed in Table 1 below.

TABLE 1

Examples of the compounds of the formula (I)

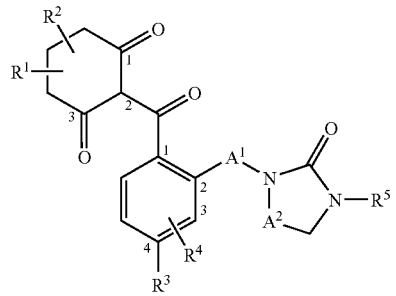
(IA)

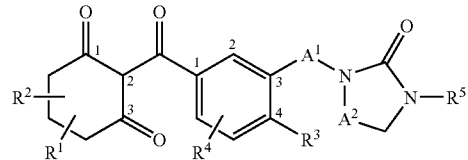
(IB)

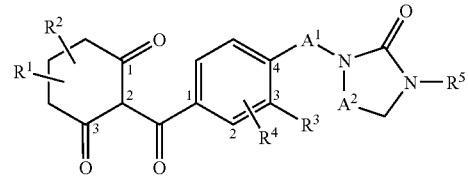
(IC)

| Ex. No. | $A^1$ | $A^2$ | (position) $R^1$ (or $R^1$ + $R^2$) | (position) $R^2$ | $R^3$ | (position) $R^4$ | $R^5$ | Formula Physical data |
|---|---|---|---|---|---|---|---|---|
| 2 | $CH_2$ | $CH_2CH_2$ | (5) $CH_3$ | H | Cl | (2) Cl | $CH_3$ | (IB) logP = 2.55[a] |
| 3 | $CH_2$ | $CH_2CH_2$ | (5) $CH_3$ | (5) $CH_3$ | Cl | (2) Cl | $CH_3$ | (IB) logP = 2.79[a] |
| 4 | $CH_2$ | $CH_2CH_2$ | (4) $CH_3$ | (4) $CH_3$ | Cl | (2) Cl | $CH_3$ | (IB) logP = 2.89[a] |
| 5 | $CH_2$ | $CH_2CH_2$ | (5) $C_3H_7$-i | H | Cl | (2) Cl | $CH_3$ | (IB) logP = 3.22[a] |
| 6 | $CH_2$ | $CH_2CH_2$ | (5) $C_6H_5$ | H | Cl | (2) Cl | $CH_3$ | (IB) logP = 3.21[a] |
| 7 | $CH_2$ | $CH_2$ | (5) $CH_3$ | H | Cl | (2) Cl | $CH_3$ | (IB) logP = 2.43[a] |
| 8 | $CH_2$ | $CH_2$ | (5) $CH_3$ | (5) $CH_3$ | Cl | (2) Cl | $CH_3$ | (IB) logP = 2.67[a] |
| 9 | $CH_2$ | $CH_2$ | (4) $CH_3$ | (4) $CH_3$ | Cl | (2) Cl | $CH_3$ | (IB) logP = 2.75[a] |
| 10 | $CH_2$ | $CH_2$ | (5) $C_3H_7$-i | H | Cl | (2) Cl | $CH_3$ | (IB) logP = 3.09[a] |
| 11 | $CH_2$ | $CH_2$ | (5) $C_6H_5$ | H | Cl | (2) Cl | $CH_3$ | (IB) logP = 3.10[a] |
| 12 | $CH_2$ | $CH_2$ | (5) $CH_3$ | H | Cl | (2) Cl | $C_2H_5$ | (IB) logP = 2.71[a] |

TABLE 1-continued

Examples of the compounds of the formula (I)

| | | | | | | | | | |
|---|---|---|---|---|---|---|---|---|---|
| 13 | CH$_2$ | CH$_2$ | H | H | Cl | (2) Cl | C$_2$H$_5$ | (IB) | logP = 2.37$^{a)}$ |
| 14 | CH$_2$ | CH$_2$ | (5) CH$_3$ | (5) CH$_3$ | Cl | (2) Cl | C$_2$H$_5$ | (IB) | logP = 2.96$^{a)}$ |
| 15 | CH$_2$ | CH$_2$ | (4) CH$_3$ | (4) CH$_3$ | Cl | (2) Cl | C$_2$H$_5$ | (IB) | logP = 3.07$^{a)}$ |
| 16 | CH$_2$ | CH$_2$ | (5) C$_3$H$_7$-i | H | Cl | (2) Cl | C$_2$H$_5$ | (IB) | logP = 3.40$^{a)}$ |
| 17 | CH$_2$ | CH$_2$ | (5) C$_6$H$_5$ | H | Cl | (2) Cl | C$_2$H$_5$ | (IB) | logP = 3.38$^{a)}$ |
| 18 | CH$_2$ | CH$_2$CH$_2$ | H | H | Cl | (2) OCH$_3$ | CH$_3$ | (IB) | logP = 2.05$^{a)}$ |
| 19 | CH$_2$ | CH$_2$ | H | H | Cl | (2) OCH$_3$ | CH$_3$ | (IB) | logP = 2.00$^{a)}$ |
| 20 | CH$_2$ | CH$_2$ | (5, 5) (CH$_2$)$_3$ | — | Cl | (2) Cl | CH$_3$ | (IB) | logP = 2.83$^{a)}$ |
| 21 | CH$_2$ | CH$_2$ | (5, 5) (CH$_2$)$_3$ | — | Cl | (2) Cl | C$_2$H$_5$ | (IB) | logP = 3.15$^{a)}$ |
| 22 | CH$_2$ | CH$_2$ | H | H | SO$_2$CH$_3$ | (2) Cl | CH$_3$ | (IB) | logP = 1.70$^{a)}$ |
| 23 | CH$_2$ | CH$_2$ | H | H | SO$_2$CH$_3$ | (2) Cl | C$_2$H$_5$ | (IB) | logP = 1.91$^{a)}$ |
| 24 | CH$_2$ | CH$_2$ | H | H | F | (2) Cl | CH$_3$ | (IB) | logP = 1.96$^{a)}$ |
| 25 | CH$_2$ | CH$_2$ | H | H | CF$_3$ | — | C$_2$H$_5$ | (IA) | logP = 2.68$^{a)}$ |
| 26 | CH$_2$ | CH$_2$ | (5) CH$_3$ | H | SO$_2$CH$_3$ | (2) Cl | CH$_3$ | (IB) | m.p. 147° C. |
| 27 | CH$_2$ | CH$_2$ | (5) CH$_3$ | (5) CH$_3$ | SO$_2$CH$_3$ | (2) Cl | CH$_3$ | (IB) | m.p. 142° C. |
| 28 | CH$_2$ | CH$_2$ | (4) CH$_3$ | (4) CH$_3$ | SO$_2$CH$_3$ | (2) Cl | CH$_3$ | (IB) | m.p. 140° C. |
| 29 | CH$_2$ | CH$_2$ | (5) C$_3$H$_7$-i | H | SO$_2$CH$_3$ | (2) Cl | CH$_3$ | (IB) | m.p. 162° C. |
| 30 | CH$_2$ | CH$_2$ | (5) C$_6$H$_5$ | H | SO$_2$CH$_3$ | (2) Cl | CH$_3$ | (IB) | m.p. 174° C. |
| 31 | CH$_2$ | CH$_2$ | (5, 5) (CH$_2$)$_3$ | — | SO$_2$CH$_3$ | (2) Cl | CH$_3$ | (IB) | m.p. 181° C. |
| 32 | CH$_2$ | CH$_2$ | (5) CH$_3$ | H | SO$_2$CH$_3$ | (2) Cl | C$_2$H$_5$ | (IB) | m.p. 40° C. |
| 33 | CH$_2$ | CH$_2$ | (5) CH$_3$ | (5) CH$_3$ | SO$_2$CH$_3$ | (2) Cl | C$_2$H$_5$ | (IB) | m.p. 160° C. |
| 34 | CH$_2$ | CH$_2$ | (4) CH$_3$ | (4) CH$_3$ | SO$_2$CH$_3$ | (2) Cl | C$_2$H$_5$ | (IB) | m.p. 166° C. |
| 35 | CH$_2$ | CH$_2$ | (5) C$_3$H$_7$-i | H | SO$_2$CH$_3$ | (2) Cl | C$_2$H$_5$ | (IB) | m.p. 144° C. |
| 36 | CH$_2$ | CH$_2$ | (5) C$_6$H$_5$ | H | SO$_2$CH$_3$ | (2) Cl | C$_2$H$_5$ | (IB) | m.p. 182° C. |
| 37 | CH$_2$ | CH$_2$ | (5, 5) (CH$_2$)$_3$ | — | SO$_2$CH$_3$ | (2) Cl | C$_2$H$_5$ | (IB) | m.p. 147° C. |
| 38 | CH$_2$ | CH$_2$CH$_2$ | H | H | Cl | (2) OCH$_3$ | C$_3$H$_7$-i | (IB) | |
| 39 | CH$_2$ | CH$_2$ | H | H | Cl | (2) Cl | C$_3$H$_7$-i | (IB) | m.p.: 109° C. |
| 40 | CH$_2$ | CH$_2$ | H | H | SO$_2$CH$_3$ | (2) Cl | C$_3$H$_7$-i | (IB) | m.p.: 135° C. |
| 41 | CH$_2$ | CH$_2$CH$_2$ | H | H | SO$_2$CH$_3$ | (2) Cl | CH$_3$ | (IB) | logP = 1.73$^{a)}$ |
| 42 | CH$_2$ | CH$_2$ | (5) CH$_3$ | H | Cl | (2) Cl | C$_3$H$_7$-i | (IB) | m.p.: 123° C. |
| 43 | CH$_2$ | CH$_2$ | (5) CH$_3$ | (5) CH$_3$ | Cl | (2) Cl | C$_3$H$_7$-i | (IB) | m.p.: 127° C. |
| 44 | CH$_2$ | CH$_2$CH$_2$ | H | H | Cl | (2) Cl | C$_3$H$_7$-i | (IB) | m.p.: 151° C. |
| 45 | CH$_2$ | CH$_2$CH$_2$ | H | H | SO$_2$CH$_3$ | (2) Cl | C$_3$H$_7$-i | (IB) | m.p.: 180° C. |

TABLE 1-continued

Examples of the compounds of the formula (I)

| | | | | | | | | |
|---|---|---|---|---|---|---|---|---|
| 46 | CH$_2$ | CH$_2$ | H | H | Cl | (2) Cl | C$_3$H$_7$-n | (IB) logP = 2.69[a) |
| 47 | CH$_2$ | CH$_2$ | H | H | Cl | (2) Cl | C$_4$H$_9$-n | (IB) logP = 3.08[a) |
| 48 | CH$_2$ | CH$_2$ | H | H | Cl | (2) Cl | C$_4$H$_9$-i | (IB) logP = 3.03[a) |
| 49 | CH$_2$ | CH$_2$CH$_2$ | H | H | CF$_3$ | — | CH$_3$ | (IA) logP = 2.59[a) |
| 50 | CH$_2$ | CH$_2$ | H | H | F | (2) Cl | C$_2$H$_5$ | (IB) logP = 2.18[a) |
| 51 | CH$_2$ | CH$_2$ | H | H | CF$_3$ | — | CH$_3$ | (IA) logP = 2.41[a) |

The logP values given in Table 1 were determined in accordance with EEC Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding test results in Table 1 are labelled [a).

(b) Mobile phases for the determination in the neutral range: 0.01 molar aqueous phosphate buffer solution, acetonitrile; linear gradient from 10% acetonitrile to 90% acetonitrile—the corresponding test results in Table 1 are labelled [b).

Calibration was carried out using unbranched alkan-2-ones (having 3 to 16 carbon atoms) with known logP values (determination of the logP values by retention times using linear interpolation between two successive alkanones).

The lambda max values were determined in the maxima of the chromatographic signals using the UV spectra from 200 nm to 400 nm.

Starting Materials of the Formula (III)

Example (III-1)

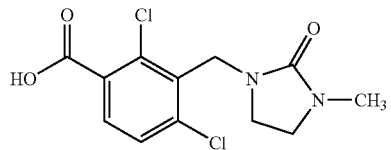

At room temperature (approximately 20° C.), a mixture of 29 g (88 mmol) of methyl 2,4-dichloro-3-[(3-methyl-2-oxo-imidazolidin-1-yl)-methyl]-benzoate, 3.6 g (90 mmol) of sodium hydroxide, 50 ml of water and 100 ml of 1,4-dioxane is stirred for 15 hours and then concentrated under water-pump vacuum. The residue is taken up in 100 ml of water and, with stirring, acidified with 2N hydrochloric acid. The resulting crystalline product is isolated by filtration with suction.

This gives 25.1 g (94% of theory) of 2,4-dichloro-3-[(3-methyl-2-oxo-imidazolidin-1-yl)-methyl]-benzoic acid of melting point 221° C.

Analogously to Example (III-1), it is also possible to prepare, for example, the compounds of the general formula (III) listed in Table 2 below:

TABLE 2

Examples of the compounds of the formula (III)

(III)

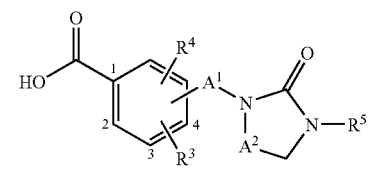

| Ex. No. | (position) A$^1$ | A$^2$ | (position) R$^3$ | (position) R$^4$ | R$^5$ | Physical data |
|---|---|---|---|---|---|---|
| III-2 | (3) CH$_2$ | CH$_2$ | (2) Cl | (4) Cl | C$_2$H$_5$ | m.p.: 228° C. |
| III-3 | (3) CH$_2$ | CH$_2$ | (2) Cl | (4) SO$_2$CH$_3$ | C$_2$H$_5$ | m.p.: 223° C. |
| III-4 | (3) CH$_2$ | CH$_2$ | (2) Cl | (4) SO$_2$CH$_3$ | CH$_3$ | m.p.: 214° C. |
| III-5 | (3) CH$_2$ | CH$_2$ | (2) OCH$_3$ | (4) Cl | CH$_3$ | m.p.: 184° C. |
| III-6 | (3) CH$_2$ | CH$_2$CH$_2$ | (2) Cl | (4) Cl | CH$_3$ | m.p.: 240° C. |

TABLE 2-continued

Examples of the compounds of the formula (III)

(III)

| Ex. No. | (position) A¹ | A² | (position) R³ | (position) R⁴ | R⁵ | Physical data |
|---|---|---|---|---|---|---|
| III-7 | (2) CH₂ | CH₂CH₂ | (4) CF₃ | — | CH₃ | logP = 1.97[a] |
| III-8 | (2) CH₂ | CH₂ | (4) CF₃ | — | CH₃ | |
| III-9 | (3) CH₂ | CH₂ | (2) Cl | (4) F | CH₃ | logP = 1.25[a] |
| III-10 | (3) CH₂ | CH₂CH₂ | (2) OCH₃ | (4) Cl | CH₃ | logP = 1.78[a] |
| III-11 | (2) CH₂ | CH₂ | (4) CF₃ | — | C₂H₅ | ¹H-NMR (DMSO-D6 δ): 4.65 ppm (s, 2H) |
| III-12 | (3) CH₂ | CH₂ | (2) Cl | (4) Cl | i-C₃H₇ | m.p.: 163° C. |
| III-13 | (3) CH₂ | CH₂ | (2) Cl | (4) Cl | cyclopropyl | |
| III-14 | (3) CH₂ | CH₂ | (2) Cl | (4) Cl | cyclopropyl-CH₂ | |
| III-15 | (3) CH₂ | CH₂ | (2) Cl | (4) Cl | t-C₄H₉ | |
| III-16 | (3) CH₂ | CH₂ | (2) Cl | (4) Cl | NH₂ | |
| III-17 | (3) CH₂ | CH₂ | (2) Cl | (4) SO₂CH₃ | i-C₃H₇ | m.p.: 276° C. |
| III-18 | (3) CH₂ | CH₂ | (2) Cl | (4) SO₂CH₃ | cyclopropyl | |
| III-19 | (3) CH₂ | CH₂ | (2) Cl | (4) SO₂CH₃ | cyclopropyl-CH₂ | |
| III-20 | (3) CH₂ | CH₂ | (2) Cl | (4) SO₂CH₃ | t-C₄H₉ | |
| III-21 | (3) CH₂ | CH₂ | (2) Cl | (4) SO₂CH₃ | NH₂ | |
| III-22 | (3) CH₂ | CH₂ | (2) OCH₃ | (4) Cl | C₂H₅ | |
| III-23 | (3) CH₂ | CH₂ | (2) OCH₃ | (4) Cl | i-C₃H₇ | |
| III-24 | (3) CH₂ | CH₂ | (2) OCH₃ | (4) Cl | cyclopropyl | |
| III-25 | (3) CH₂ | CH₂ | (2) OCH₃ | (4) Cl | cyclopropyl-CH₂ | |
| III-26 | (3) CH₂ | CH₂ | (2) OCH₃ | (4) Cl | t-C₄H₉ | |
| III-27 | (3) CH₂ | CH₂ | (2) OCH₃ | (4) Cl | NH₂ | |

TABLE 2-continued

Examples of the compounds of the formula (III)

(III)

| Ex. No. | (position) A¹ | A² | (position) R³ | (position) R⁴ | R⁵ | Physical data |
|---|---|---|---|---|---|---|
| III-28 | (3) CH₂ | CH₂ | (2) Cl | (4) F | C₂H₅ | |
| III-29 | (3) CH₂ | CH₂ | (2) Cl | (4) F | i-C₃H₇ | |
| III-30 | (3) CH₂ | CH₂ | (2) Cl | (4) F | 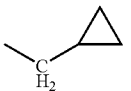 | |
| III-31 | (3) CH₂ | CH₂ | (2) Cl | (4) F |  | |
| III-32 | (3) CH₂ | CH₂ | (2) Cl | (4) F | t-C₄H₉ | |
| III-33 | (3) CH₂ | CH₂ | (2) Cl | (4) F | NH₂ | |
| III-34 | (3) CH₂ | CH₂CH₂ | (2) Cl | (4) F | C₂H₅ | |
| III-35 | (3) CH₂ | CH₂CH₂ | (2) Cl | (4) Cl | i-C₃H₇ | m.p.: 196° C. |
| III-36 | (3) CH₂ | CH₂CH₂ | (2) Cl | (4) Cl | 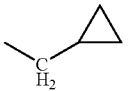 | |
| III-37 | (3) CH₂ | CH₂CH₂ | (2) Cl | (4) Cl |  | |
| III-38 | (3) CH₂ | CH₂CH₂ | (2) Cl | (4) Cl | t-C₄H₉ | |
| III-39 | (3) CH₂ | CH₂CH₂ | (2) Cl | (4) Cl | NH₂ | |
| III-40 | (3) CH₂ | CH₂CH₂ | (2) Cl | (4) SO₂CH₃ | C₂H₅ | |
| III-41 | (3) CH₂ | CH₂CH₂ | (2) Cl | (4) SO₂CH₃ | i-C₃H₇ | |
| III-42 | (3) CH₂ | CH₂CH₂ | (2) Cl | (4) SO₂CH₃ | 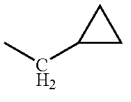 | |
| III-43 | (3) CH₂ | CH₂CH₂ | (2) Cl | (4) SO₂CH₃ | | |
| III-44 | (3) CH₂ | CH₂CH₂ | (2) Cl | (4) SO₂CH₃ | t-C₄H₉ | |
| III-45 | (3) CH₂ | CH₂CH₂ | (2) Cl | (4) SO₂CH₃ | NH₂ | |
| III-46 | (3) CH₂ | CH₂CH₂ | (2) Cl | (4) SO₂CH₃ | CH₃ | m.p.: 243° C. |
| III-47 | (2) CH₂ | CH₂CH₂ | (4) CF₃ | — | C₂H₅ | |
| III-48 | (2) CH₂ | CH₂CH₂ | (4) CF₃ | — | i-C₃H₇ | |

TABLE 2-continued

Examples of the compounds of the formula (III)

(III)

| Ex. No. | (position) A¹ | A² | (position) R³ | (position) R⁴ | R⁵ | Physical data |
|---|---|---|---|---|---|---|
| III-49 | (2) CH₂ | CH₂CH₂ | (4) CF₃ | — | 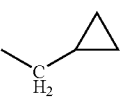 | |
| III-50 | (2) CH₂ | CH₂CH₂ | (4) CF₃ | — |  | |
| III-51 | (2) CH₂ | CH₂CH₂ | (4) CF₃ | — | t-C₄H₉ | |
| III-52 | (2) CH₂ | CH₂CH₂ | (4) CF₃ | — | NH₂ | |
| III-53 | (2) CH₂ | CH₂ | (4) CF₃ | — | i-C₃H₇ | |
| III-54 | (2) CH₂ | CH₂ | (4) CF₃ | — | 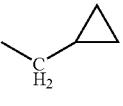 | |
| III-55 | (2) CH₂ | CH₂ | (4) CF₃ | — |  | |
| III-56 | (2) CH₂ | CH₂ | (4) CF₃ | — | t-C₄H₉ | |
| III-57 | (2) CH₂ | CH₂ | (4) CF₃ | — | NH₂ | |
| III-58 | (3) CH₂ | CH₂CH₂ | (2) OCH₃ | (4) Cl | C₂H₅ | |
| III-59 | (3) CH₂ | CH₂CH₂ | (2) OCH₃ | (4) Cl | i-C₃H₇ | |
| III-60 | (3) CH₂ | CH₂CH₂ | (2) OCH₃ | (4) Cl | 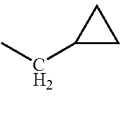 | |
| III-61 | (3) CH₂ | CH₂CH₂ | (2) OCH₃ | (4) Cl |  | |
| III-62 | (3) CH₂ | CH₂CH₂ | (2) OCH₃ | (4) Cl | t-C₄H₉ | |
| III-63 | (3) CH₂ | CH₂CH₂ | (2) OCH₃ | (4) Cl | NH₂ | |
| III-64 | (2) CH₂ | CH₂CH₂ | (4) CN | — | CH₃ | |
| III-65 | (2) CH₂ | CH₂CH₂ | (4) CN | — | C₂H₅ | |
| III-66 | (2) CH₂ | CH₂CH₂ | (4) CN | — | i-C₃H₇ | |
| III-67 | (2) CH₂ | CH₂CH₂ | (4) CN | — | 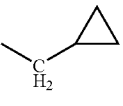 | |
| III-68 | (2) CH₂ | CH₂CH₂ | (4) CN | — |  | |

TABLE 2-continued

Examples of the compounds of the formula (III)

(III)

| Ex. No. | (position) A$^1$ | A$^2$ | (position) R$^3$ | (position) R$^4$ | R$^5$ | Physical data |
|---|---|---|---|---|---|---|
| III-69 | (2) CH$_2$ | CH$_2$CH$_2$ | (4) CN | — | t-C$_4$H$_9$ | |
| III-70 | (2) CH$_2$ | CH$_2$CH$_2$ | (4) CN | — | NH$_2$ | |
| III-71 | (2) CH$_2$ | CH$_2$ | (4) CN | — | CH$_3$ | |
| III-72 | (2) CH$_2$ | CH$_2$ | (4) CN | — | C$_2$H$_5$ | |
| III-73 | (2) CH$_2$ | CH$_2$ | (4) CN | — | i-C$_3$H$_7$ | |
| III-74 | (2) CH$_2$ | CH$_2$ | (4) CN | — |  | |
| III-75 | (2) CH$_2$ | CH$_2$ | (4) CN | — | 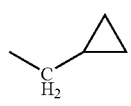 | |
| III-76 | (2) CH$_2$ | CH$_2$ | (4) CN | — | t-C$_4$H$_9$ | |
| III-77 | (2) — | CH$_2$ | (4) Cl | — | CH$_3$ | |
| III-78 | (2) — | CH$_2$ | (4) SO$_2$CH$_3$ | — | CH$_3$ | |
| III-79 | (2) — | CH$_2$CH$_2$ | (4) Cl | — | CH$_3$ | |
| III-80 | (2) — | CH$_2$CH$_2$ | (4) SO$_2$CH$_3$ | — | CH$_3$ | |
| III-81 | (3) — | CH$_2$ | (2) Cl | (4) Cl | CH$_3$ | |
| III-82 | (3) — | CH$_2$ | (2) Cl | (4) SO$_2$CH$_3$ | CH$_3$ | |
| III-83 | (3) — | CH$_2$CH$_2$ | (2) Cl | (4) Cl | CH$_3$ | |
| III-84 | (3) — | CH$_2$CH$_2$ | (2) Cl | (4) SO$_2$CH$_3$ | CH$_3$ | |
| III-85 | (3) — | CH$_2$ | (2) OCH$_3$ | (4) Cl | CH$_3$ | |
| III-86 | (3) — | CH$_2$CH$_2$ | (2) OCH$_3$ | (4) Cl | CH$_3$ | |
| III-87 | (2) CH$_2$CH$_2$ | CH$_2$ | (4) Cl | — | CH$_3$ | |
| III-88 | (2) CH$_2$CH$_2$ | CH$_2$CH$_2$ | (4) Cl | — | CH$_3$ | |
| III-89 | (2) CH$_2$CH$_2$ | CH$_2$ | (4) CF$_3$ | — | CH$_3$ | |
| III-90 | (2) CH$_2$CH$_2$ | CH$_2$CH$_2$ | (4) CF$_3$ | — | CH$_3$ | |
| III-91 | (2) — | CH$_2$ | (4) CF$_3$ | — | CH$_3$ | |
| III-92 | (2) — | CH$_2$CH$_2$ | (4) CF$_3$ | — | CH$_3$ | |
| III-93 | (2) CH$_2$CH$_2$ | CH$_2$ | (2) Cl | (4) Cl | CH$_3$ | |
| III-94 | (2) CH$_2$CH$_2$ | CH$_2$CH$_2$ | (2) Cl | (4) Cl | CH$_3$ | |
| III-95 | (2) CH$_2$CH$_2$ | CH$_2$ | (2) Cl | (4) SO$_2$CH$_3$ | CH$_3$ | |
| III-96 | (2) CH$_2$CH$_2$ | CH$_2$CH$_2$ | (2) Cl | (4) SO$_2$CH$_3$ | CH$_3$ | |

TABLE 2-continued

Examples of the compounds of the formula (III)

(III)

| Ex. No. | (position) $A^1$ | $A^2$ | (position) $R^3$ | (position) $R^4$ | $R^5$ | Physical data |
|---|---|---|---|---|---|---|
| III-97 | (3) $CH_2$ | $CH_2$ | (2) Cl | (4) Cl | $C_3H_7$-n | m.p.: 195° C. |
| III-98 | (3) $CH_2$ | $CH_2$ | (2) Cl | (4) Cl | $C_4H_9$-n | m.p.: 163° C. |
| III-99 | (3) $CH_2$ | $CH_2$ | (2) Cl | (4) Cl | $C_4H_3$-i | m.p.: 195° C. |

Intermediates of the Formula (IV)

Example (IV-1)

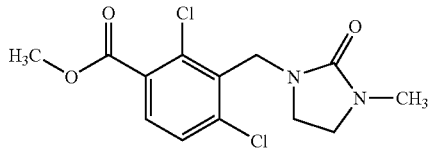

A mixture of 20 g (0.20 mol) of 1-methyl-2-oxo-imidazolidine, 30 g (0.10 mol) of methyl 3-bromomethyl-2,4-dichloro-benzoate, 53 g (0.50 mol) of potassium carbonate and 400 ml of acetonitrile is heated at reflux with stirring for 48 hours. 1 g of sodium iodide is added, and the mixture is then heated at reflux for a further 48 hours and subsequently filtered. Under reduced pressure, the solvent is carefully distilled off from the filtrate. The residue is purified by column chromatography (silica gel, ethyl acetate).

This gives 29.1 g (92% of theory) of methyl 2,4-dichloro-3-[(3-methyl-2-oxo-imidazolidin-1-yl)-methyl]-benzoate of melting point 59° C.

Analogously to Example (IV-1), it is also possible to prepare, for example, the compounds of the general formula (IV) listed in Table 3 below—and also, for example, the methyl esters of the benzoic acids listed above in Table 2:

TABLE 3

Examples of the compounds of the formula (IV)

(IV)

| Ex. No. | (position) $A^1$ | $A^2$ | R | (position) $R^3$ | (position) $R^4$ | $R^5$ | Physical data |
|---|---|---|---|---|---|---|---|
| IV-2 | (3) $CH_2$ | $CH_2$ | $CH_3$ | (2) Cl | (4) Cl | $C_2H_5$ | logP = 2.26[a] |
| IV-3 | (3) $CH_2$ | $CH_2$ | $CH_3$ | (2) Cl | (4) $SO_2CH_3$ | $C_2H_5$ | logP = 1.55[a] |
| IV-4 | (3) $CH_2$ | $CH_2$ | $CH_3$ | (2) Cl | (4) $SO_2CH_3$ | $CH_3$ | logP = 1.55[a] |
| IV-5 | (3) $CH_2$ | $CH_2$ | $CH_3$ | (2) $OCH_3$ | (4) Cl | $CH_3$ | logP = 1.92[a] |
| IV-6 | (3) $CH_2$ | $CH_2CH_2$ | $CH_3$ | (2) Cl | (4) Cl | $CH_3$ | logP = 2.07[a] |
| IV-7 | (2) $CH_2$ | $CH_2CH_2$ | $CH_3$ | (4) $CF_3$ | — | $CH_3$ | |
| IV-8 | (2) $CH_2$ | $CH_2$ | $CH_3$ | (4) $CF_3$ | — | $CH_3$ | |
| IV-9 | (3) $CH_2$ | $CH_2CH_2$ | $CH_3$ | (2) Cl | (4) F | $CH_3$ | |

TABLE 3-continued

Examples of the compounds of the formula (IV)

(IV)

[Structure: R-O-C(=O)-phenyl(R4, R3)-A1-N-C(=O)-N(R5)-A2 cyclic urea]

| Ex. No. | (position) A$^1$ | A$^2$ | R | (position) R$^3$ | (position) R$^4$ | R$^5$ | Physical data |
|---|---|---|---|---|---|---|---|
| IV-10 | (3) CH$_2$ | CH$_2$CH$_2$ | CH$_3$ | (2) OCH$_3$ | (4) Cl | CH$_3$ | logP = 2.03$^{a)}$ |
| IV-11 | (2) CH$_2$ | CH$_2$ | CH$_3$ | (4) CF$_3$ | — | C$_2$H$_5$ | logP = 2.62$^{a)}$ |
| IV-12 | (3) CH$_2$ | CH$_2$ | CH$_3$ | (2) Cl | (4) Cl | C$_3$H$_7$-n | logP = 2.62 |
| IV-13 | (3) CH$_2$ | CH$_2$ | CH$_3$ | (2) Cl | (4) Cl | C$_3$H$_7$-i | logP = 2.56 |
| IV-14 | (3) CH$_2$ | CH$_2$ | CH$_3$ | (2) Cl | (4) SO$_2$CH$_3$ | C$_3$H$_7$-i | $^1$H-NMR (CD$_3$CN) δ = 1.07(d, 6H); 3.20(s, SO$_2$CH$_3$); 3.92(s, OCH$_3$); 4.91(CH$_2$); 7.76(d, 2H); 8.10(d, 2H) ppm |
| IV-15 | (3) CH$_2$ | CH$_2$ | CH$_3$ | (2) Cl | (4) Cl | C$_4$H$_9$-n | logP = 3.0 |
| IV-16 | (3) CH$_2$ | CH$_2$ | CH$_3$ | (2) Cl | (4) Cl | C$_4$H$_9$-i | logP = 2.95 |
| IV-17 | (3) CH$_2$ | CH—CH$_2$ | CH$_3$ | (2) Cl | (4) SO$_2$CH$_3$ | CH$_3$ | LC-MS: M + 1 = 375/7 |
| IV-18 | (3) CH$_2$ | CH—CH$_2$ | CH$_3$ | (2) Cl | (4) Cl | C$_3$H$_7$-i | logP = 2.65 |

Intermediates of the Formula (V)

The halogenoalkylbenzoic esters of the general formula (V) can be prepared in a known manner by halogenation of the corresponding alkylbenzoic esters using, for example, N-bromo-succinimide or N-chloro-succinimide.

Examples of the haiogenoalkylbenzoic esters of the formula (V) are listed in Table 4 below.

TABLE 4

Examples of the compounds of the formula (V)

(V)

[Structure: R-O-C(=O)-phenyl(R4, R3)-A1-X]

| Ex. No. | (position) A$^1$X | (position) R$^3$ | (position) R$^4$ | R | Physical data |
|---|---|---|---|---|---|
| V-1 | (3) CH$_2$Br | (2) Cl | (4) Cl | CH$_3$ | m.p.: 61° C. |
| V-2 | (3) CH$_2$Br | (2) Cl | (4) SO$_2$CH$_3$ | CH$_3$ | logP = 2.33$^{a)}$ |
| V-3 | (2) CH$_2$Br | (4) NO$_2$ | — | C$_2$H$_5$ | $^1$H-NMR (CDCl$_3$, δ): 4.97 ppm (s, CH$_2$) |
| V-4 | (2) CH$_2$Br | (4) CF$_3$ | — | CH$_3$ | |
| V-5 | (2) CH$_2$Br | (4) SO$_2$CH$_3$ | — | C$_2$H$_5$ | $^1$H-NMR (CDCl$_3$, δ): 4.96 ppm (s, CH$_2$) |
| V-6 | (2) CH$_2$Br | (4) SO$_2$CH$_3$ | — | CH$_3$ | logP = 1.87$^{a)}$ |
| V-7 | (2) CH$_2$Br | (4) CF$_3$ | — | C$_2$H$_5$ | $^1$H-NMR (CDCl$_3$, δ): 4.96 ppm (s, CH$_2$) |
| V-8 | (2) CH$_2$Br | (4) F | — | C$_2$H$_5$ | $^1$H-NMR (CDCl$_3$, δ): 4.93 ppm (s, CH$_2$) |
| V-9 | (2) CH$_2$Br | (4) Cl | — | C$_2$H$_5$ | $^1$H-NMR (CDCl$_3$, δ): 4.90 ppm (s, CH$_2$) |

TABLE 4-continued

Examples of the compounds of the formula (V)

(V)

R—O—C(=O)—[phenyl with R³, R⁴, A¹—X]

| Ex. No. | (position) A¹X | (position) R³ | (position) R⁴ | R | Physical data |
|---|---|---|---|---|---|
| V-10 | (2) CH₂Br | (4) Br | — | C₂H₅ | ¹H-NMR (CDCl₃, δ): 4.90 ppm (s, CH₂) |
| V-11 | (2) CH₂Br | (4) OCH₃ | — | C₂H₅ | |
| V-12 | (2) CH₂Br | (4) I | — | CH₃ | |
| V-13 | (3) CH₂Br | (2) OCH₃ | (4) Cl | CH₃ | ¹H-NMR (DMSO-D6, δ): 4.72 ppm (s, CH₂) |
| V-14 | (3) CH₂Br | (2) OCH₃ | (4) SO₂CH₃ | CH₃ | |
| V-15 | (3) CH₂Br | (2) OCH₃ | (4) CF₃ | CH₃ | |
| V-16 | (3) CH₂Br | (2) OCH₃ | (4) SCH₃ | CH₃ | |
| V-17 | (3) CH₂Br | (2) NO₂ | (4) CF₃ | CH₃ | |
| V-18 | (3) CH₂Br | (2) NO₂ | (4) SO₂CH₃ | CH₃ | |
| V-19 | (3) CH₂Br | (2) NO₂ | (4) CN | CH₃ | |
| V-20 | (2) CH₂Br | (4) CN | — | CH₃ | |
| V-21 | (3) CH₂Br | (2) CF₃ | (4) SO₂CH₃ | CH₃ | |
| V-22 | (3) CH₂Br | (2) CF₃ | (4) CN | CH₃ | |
| V-23 | (3) CH₂Br | (2) Cl | (4) F | CH₃ | |
| V-24 | (3) CH₂Br | (2) F | (4) Cl | CH₃ | |
| V-25 | (3) CH₂Br | (2) SO₂CH₃ | (4) Cl | CH₃ | |
| V-26 | (4) CH₂Br | (2) Cl | — | CH₃ | |
| V-27 | (2) CH₂Br | (4) Cl | (3) OCH₃ | CH₃ | |

Intermediates of the Formula (VI)

Example (VI-1)

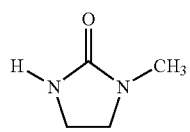

75 g (1.0 mol) of N¹-methyl-ethane-1,2-diamine are added dropwise with stirring to a mixture of 214 g (1.0 mol) of diphenyl carbonate and 1 litre of toluene. The mixture is then heated under reflux to the boil for 60 minutes and subsequently concentrated at 100° C./30 mbar. The residue is distilled at 110° C./1 mbar and the distillate (41.5% 1-methyl-2-oxo-imidazolidine and 58.5% of phenol) is purified by column chromatography (silica gel, ethyl acetate).

This gives 37.3 g (37% of theory) of 1-methyl-2-oxo-imidazolidine of melting point 114° C.

Analogously to Example (VI-1), it is also possible to prepare, for example, the compounds of the general formula (VI) listed in Table 5 below.

TABLE 5

Examples of the compounds of the formula (VI)

(VI)

[imidazolidinone structure with H—N, A², N—R⁵, C=O]

| Ex. No. | A² | R⁵ | Physical data |
|---|---|---|---|
| (VI-2) | CH₂ | C₂H₅ | m.p.: 50° C. |
| (VI-3) | CH₂ | i-C₃H₇ | m.p.: 107° C. |
| (VI-4) | CH₂ | NH₂ | m.p.: 110° C. |
| (VI-5) | CH₂ | n-C₃H₇ | oil, logP = 0.55[a)] |
| (VI-6) | CH₂ | t-C₄H₉ | m.p.: 135° C. |
| (VI-7) | CH₂ | cyclopropyl | b.p.: 92–99° C. (0.1 torr) |
| (VI-8) | CH₂CH₂ | i-C₃H₇ | m.p.: 160° C. |
| (VI-9) | CH₂CH₂ | C₂H₅ | |
| (VI-10) | CH₂CH₂ | CH₃ | m.p.: 88° C. |
| (VI-11) | CH₂CH₂ | cyclohexyl | m.p.: 197° C. |
| (VI-12) | CH₂ | cyclohexyl | m.p.: 166–168° C. |
| (VI-13) | CH₂CH₂ | NH₂ | |
| (VI-14) | CH₂CH₂ | cyclopropyl | |
| (VI-15) | CH₂CH₂ | n-C₃H₇ | logP = 0.76[a)] m.p.: 40° C. |
| (VI-16) | CH₂ | phenyl | m.p.: 163° C. |
| (VI-17) | CH₂CH₂ | phenyl | m.p.: 215° C. |
| (VI-18) | CH₂ | 4-Cl-phenyl | m.p.: 178° C. |
| (VI-19) | CH₂CH₂ | 4-Cl-phenyl | m.p.: 166–168° C. |
| (VI-20) | CH₂ | SO₂CH₃ | m.p.: 193° C. |

TABLE 5-continued

Examples of the compounds of the formula (VI)

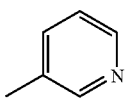

(VI)

| Ex. No. | A² | R⁵ | Physical data |
|---|---|---|---|
| (VI-21) | $CH_2CH_2$ | $SO_2CH_3$ | |
| (VI-22) | $CH_2$ | 3-pyridylmethyl | m.p.: 158.5–160.5° C. |
| (VI-23) | $CH_2CH_2$ | 3-pyridylmethyl | |
| (VI-24) | $CH_2$ | 2-pyrimidinylmethyl | |
| (VI-25) | $CH_2CH_2$ | 2-pyrimidinylmethyl | |
| (VI-26) | $CH$—$CH_2$ | $CH_2$—$C_3H_7$-i | m.p.: 121° C. |
| (VI-27) | $CH$—$CH_2$ | $C_4H_9$-n | m.p.: 63° C. |
| (VI-28) | $CH_2$ | $C_4H_9$-n | m.p.: 55° C. |
| (VI-29) | $CH_2$ | $CH_2$—$C_3H_7$-i | m.p.: 40° C. |
| (VI-30) | $CH_2$—$CH_2$—$CH_2$ | $C_2H_5$ | logP = 1.09 |
| (VI-31) | $CH_2$ | $CH_2$—$CH_2$-phenyl | m.p.: 143° C. |
| (VI-32) | $CH_2$—$CH_2$—$CH_2$ | $CH_3$ | |
| (VI-33) | $CH_2$—$CH_2$—$CH_2$ | $C_3H_7$-n | |
| (VI-34) | $CH_2$—$CH_2$—$CH_2$ | $C_3H_7$-i | |
| (VI-35) | $CH_2$—$CH_2$—$CH_2$ | cyclopropyl | |
| (VI-36) | $CH_2$—$CH_2$—$CH_2$ | $C_4H_9$-t | |

Use Examples

Example A

Pre-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:
0%=no effect (like untreated control)
100%=total destruction In this test, for example, the compounds according to Preparation Examples 1, 2, 3, 4, 7, 8, 9, 12, 13, 18 and 24 show strong activity against weeds.

Example B

Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction In this test, for example, the compounds of Preparation Examples 1, 2, 3, 4, 5, 6, 7, 8, 9, 10, 11, 12, 13, 14, 16, 17, 18 and 24 show strong activity against weeds.

The foregoing examples of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A substituted benzoylcyclohexanedione of formula (I)

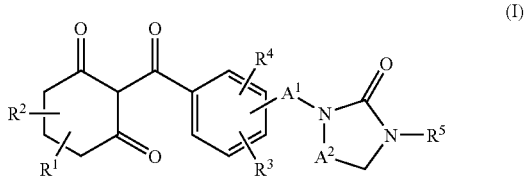

(I)

or tautomeric forms thereof or agrochemically acceptable salts thereof,
wherein
  A¹ represents a single bond or represents alkanediyl (alkylene) having 1 to 3 carbon atoms,
  A² represents ethane-1,2-diyl or propane-1,2-diyl,
  R¹ represents hydrogen, represents phenyl or represents optionally halogen-substituted alkyl, alkylthio or alkoxycarbonyl having in each case 1 to 4 carbon atoms in the alkyl groups,
  R² represents hydrogen or represents optionally halogen-substituted alkyl or alkylthio having in each case 1 to 4 carbon atoms, or together with R¹ represents alkanediyl (alkylene) having up to 4 carbon atoms, or—if $R^1$ and $R^2$ are attached to the same carbon atom—together with $R^1$ and the carbon atom to which $R^1$ and $R^2$ are attached represents a carbonyl grouping (C=O), $R^3$ represents hydrogen, nitro, cyano, carboxyl, carbamoyl, thiocarbamoyl, halogen, represents optionally halogen-substituted alkyl, alkoxy, alkylthio, alkylsulphinyl, alkylsulphonyl, alkylamino, dialkylamino, alkylsulphonylamino or dialkylaminosulphonyl having in each case 1 to 4 carbon atoms in the alkyl groups, or represents optionally halogen- or $C_1$-$C_4$-alkyl-substituted cycloalkylamino, cycloalkylsulphonyl, cycloalkylsulphonylamino or cycloalkylaminosulphonyl having in each case 3 to 6 carbon atoms, $R^4$ represents hydrogen, nitro, cyano, carboxyl, carbamoyl, thiocarbamoyl, halogen, or represents optionally halogen-substituted alkyl, alkoxy, alkylthio, alkylsulphinyl, alkylsulphonyl, alkylamino, dialkylamino or dialkylaminosulphonyl having in each case 1 to 4 carbon atoms in the alkyl groups, and $R^5$ represents hydrogen, represents amino, represents optionally amino-, cyano-, halogen- or $C_1$-$C_4$-alkoxy-substituted alkyl, alkoxy, alkylamino, dialkylamino, alkylsulphonyl or alkylsulphonylamino having in each case 1 to 5 carbon atoms in the alkyl groups, represents optionally halogen-substituted alkenyl or alkynyl having in each case up to 5 carbon atoms, represents optionally cyano-, halogen- or $C_1$-$C_4$-alkyl-substituted cycloalkyl or cycloalkylalkyl having in each case 3 to 6 carbon atoms in the cycloalkyl group and optionally 1 to 3 carbon atoms in the alkyl moiety, represents cycloalkenyl having 5 or 6 carbon atoms, or represents optionally nitro-, cyano-, carboxyl-, halogen-, $C_1$-$C_4$-alkyl-, $C_1$-$C_4$-halogenoalkyl-, $C_1$-$C_4$-alkoxy- or $C_1$-$C_4$-halogenoalkoxy-substituted phenyl, phenyl-$C_1$-$C_4$-alkyl, pyridyl or pyrimidinyl, except for the compound 1-[2,6-dichloro-3-[(2-hydroxy-6-oxo-cyclohexen-1-yl)-carbonyl]-benzyl]-3-methyl-tetrahydro-2(1H)-pyrimidinone.

2. The compound of claim 1 wherein $A^1$ represents a single bond, represents methylene, ethane-1,1-diyl (ethylidene), ethane-1,2-diyl (dimethylene), propane-1,1-diyl, propane-1,2-diyl or propane-1,3-diyl, $A^2$ represents ethane-1,2-diyl or propane-1,2-diyl, $R^1$ represents hydrogen, represents phenyl or represents optionally fluorine and/or chlorine-substituted methyl, ethyl, n- or i-propyl, methylthio, ethylthio, n- or i-propylthio, methoxycarbonyl, ethoxycarbonyl, n- or i-propoxycarbonyl, $R^2$ represents hydrogen or represents optionally fluorine- and/or chlorine-substituted methyl, ethyl, n- or i-propyl, methylthio, ethylthio, n- or i-propylthio, or together with $R^1$ represents methylene, ethane-1,1-diyl, ethane-1,2-diyl (dimethylene), propane-1,1-diyl, propane-1,2-diyl or propane-1,3-diyl, or—if $R^1$ and $R^2$ are attached to the same carbon atom—together with $R^1$ and the carbon atom to which $R^1$ and $R^2$ are attached represents a carbonyl grouping (C=O), $R^3$ represents hydrogen, nitro, cyano, carboxyl, carbamoyl, thiocarbamoyl, fluorine, chlorine, bromine, iodine, represents optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino, diethylamino, methylsulphonylamino, ethylsulphonylamino, n- or i-propylsulphonylamino, dimethylaminosulphonyl or diethylaminosulphonyl, or represents optionally fluorine-, chlorine- or methyl-substituted cyclopropylamino, cyclobutylamino, cyclopentylamino, cyclohexylamino, cyclopropylsulphonyl, cyclobutylsulphonyl, cyclopentylsulphonyl, cyclohexylsulphonyl, cyclopropylsulphonylamino, cyclobutylsulphonylamino, cyclopentylsulphonylamino, cyclohexylsulphonylamino, cyclopropylaminosulphonyl, cyclobutylaminosulphonyl, cyclopentylaminosulphonyl or cyclohexylaminosulphonyl, $R^4$ represents hydrogen, nitro, cyano, carboxyl, carbamoyl, thiocarbamoyl, fluorine, chlorine, bromine, iodine, or represents optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino, diethylamino, dimethylaminosulphonyl or diethylaminosulphonyl, and $R^5$ represents hydrogen, represents amino, represents optionally amino-, cyano-, fluorine- and/or chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, dipropylamino, methylsulphonyl, ethylsulphonyl or methylsulphonylamino, represents optionally fluorine-, chlorine- and/or bromine-substituted propenyl, butenyl, propynyl or butynyl, represents optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents cyclohexenyl, or represents optionally fluorine-, chlorine-, bromine-, methyl-, trifluoromethyl-, methoxy-, difluoromethoxy- or trifluoromethoxy-substituted phenyl, benzyl, pyridyl or pyrimidinyl.

3. The compound of claim 1 wherein $A^1$ represents a single bond, represents methylene, ethane-1,2-diyl (dimethylene) or propane-1,3-diyl, $A^2$ represents ethane-1,2-diyl, $R^1$ represents hydrogen, phenyl, methyl, ethyl, n- or i-propyl, methylthio, ethylthio, methoxycarbonyl or ethoxycarbonyl, $R^2$ represents hydrogen, methyl, ethyl, methylthio, ethylthio, or together with $R^1$ represents methylene, ethane-1,2-diyl (dimethylene) or propane-1,3-diyl (trimethylene), or—if $R^1$ and $R^2$ are attached to the same carbon atom—together with $R^1$ and the carbon atom to which $R^1$ and $R^2$ are attached represents a carbonyl grouping (C=O), $R^3$ represents hydrogen, nitro, cyano, fluorine, chlorine, bromine, iodine, represents optionally fluorine- and/or chlorine-substituted methyl, ethyl, methoxy, ethoxy, methylthio, ethylthio, methylsulphinyl, ethylsulphinyl, methylsulphonyl, ethylsulphonyl, represents methylamino, ethylamino, dimethylamino or dimethylaminosulphonyl, $R^4$ represents hydrogen, nitro, cyano, fluorine, chlorine, bromine, iodine, represents optionally fluorine- and/or chlorine-substituted methyl, ethyl, methoxy, ethoxy, methylthio, ethylthio, methylsulphinyl, ethylsulphinyl, methylsulphonyl, ethylsulphonyl, represents methylamino, ethylamino, dimethylamino or dimethylaminosulphonyl, and $R^5$ represents hydrogen, methyl, ethyl, n- or i-propyl, n-, i-, s- or t-butyl, propenyl, propynyl, cyclopropyl, cyclopentyl, cyclohexyl, cyclopropylmethyl, cyclopentylmethyl, cyclohexylmethyl, phenyl or benzyl.

4. The compound of claim 1 wherein
$A^1$ represents methylene or ethane-1,2-diyl (dimethylene),
$A^2$ represents ethane-1,2-diyl,
$R^1$ represents hydrogen, phenyl, methyl, ethyl, n- or i-propyl, methylthio or ethylthio,
$R^2$ represents hydrogen, methyl, ethyl, methylthio, or together with $R^1$ represents ethane-1,2-diyl or propane-1,3-diyl, or—if $R^1$ and $R^2$ are attached to the same carbon atom—together with $R^1$ and the carbon atom to which $R^1$ and $R^2$ are attached represents a carbonyl grouping (C=O),
$R^3$ represents hydrogen, nitro, cyano, fluorine, chlorine, bromine, methyl, difluoromethyl, trifluoromethyl, dichloromethyl, trichloromethyl, chlorodifluoromethyl, ethyl, methoxy, difluoromethoxy, trifluoromethoxy, chlorodifluoromethoxy, ethoxy, methylthio, difluoromethylthio, trifluoromethylthio, chlorodifluoromethylthio, ethylthio, methylsulphinyl, trifluoromethylsulphinyl, ethylsulphinyl, methylsulphonyl, trifluoromethylsulphonyl, ethylsulphonyl, dimethylamino or dimethylaminosulphonyl,
$R^4$ represents hydrogen, nitro, cyano, fluorine, chlorine, bromine, methyl, difluoromethyl, trifluoromethyl, dichloromethyl, trichloromethyl, chlorodifluoromethyl, ethyl, methoxy, difluoromethoxy, trifluoromethoxy, chlorodifluoromethoxy, ethoxy, methylthio, difluoromethylthio, trifluoromethylthio, chlorodifluoromethylthio, ethylthio, methylsulphinyl, trifluoromethylsulphinyl, ethylsulphinyl, methylsulphonyl, trifluoromethylsulphonyl, ethylsulphonyl, dimethylamino or dimethylaminosulphonyl, and
$R^5$ represents hydrogen, methyl, ethyl, n- or i-propyl, n-, i-, s- or t-butyl, cyclopropyl, cyclopentyl or cyclohexyl.

5. A compound consisting of the sodium, potassium, magnesium, calcium, ammonium, $C_1$-$C_4$-alkyl-ammonium, di($C_1$-$C_4$-alkyl)-ammonium, tri($C_1$-$C_4$-alkyl)ammonium, tetra-($C_1$-$C_4$-alkyl)-ammonium, tri($C_1$-$C_4$-alkyl)sulphonium, $C_5$- or $C_6$-cycloalkyl-ammonium or di($C_1$-$C_2$-alkyl) benzyl-ammonium salt of the formula (I), wherein $A^1$, $A^2$, $R^3$, $R^4$ and $R^5$ are as defined in claim 1.

6. The compound of claim 4 having the formulae (IA), (IB) or (IC)

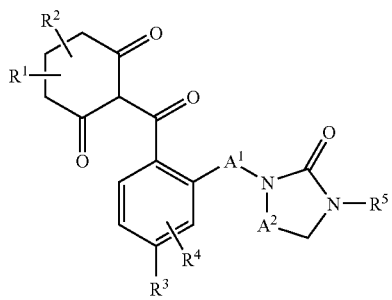
(IA)

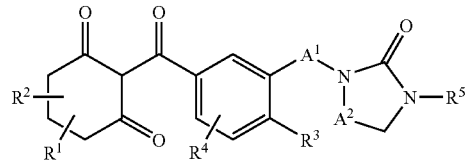
(IB)

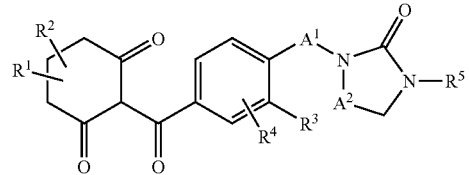
(IC)

wherein $A^1$, $A^2$, $R^1$, $R^2$, $R^3$, $R^4$, and $R^5$ are as defined in claim 4.

7. A process for preparing the substituted benzoylcyclohexanedione of claim 1 comprising reacting a 1,3-cyclohexanedione of the formula (II)

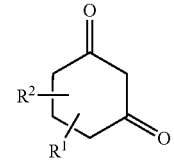
(II)

wherein $R^1$ and $R^2$ are as defined in claim 1,
with a substituted benzoic acid of the formula (III)

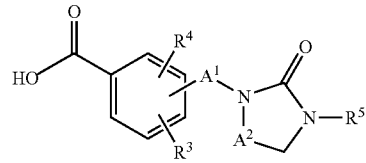
(III)

wherein $A^1$, $A^2$, $R^3$, $R^4$ and $R^5$ are as defined in claim 1, in the presence of a dehydrating agent, optionally in the presence of one or more reaction auxiliaries and optionally in the presence of a diluent.

8. A method for controlling plant growth comprising applying an effective amount of at least one compound of claim 1 to the plant and/or its habitat.

9. A composition comprising at least one compound of claim 1 and at least one of extenders and surfactants.

* * * * *